United States Patent [19]
Zweng et al.

[11] 3,963,939
[45] June 15, 1976

[54] ANALYZING GASES BY TESTING THE OPTICAL CHARACTERISTICS OF EXHAUST GASES FROM INTERNAL COMBUSTION ENGINES

[75] Inventors: Josef Zweng, Warmbronn; Iwan Komaroff, Regensburg, both of Germany

[73] Assignee: Robert Bosch G.m.b.H., Gerlingen-Schillerhohe, Germany

[22] Filed: Aug. 27, 1975

[21] Appl. No.: 608,277

[30] Foreign Application Priority Data
Sept. 7, 1974 Germany............................ 2442968

[52] U.S. Cl.................................. 250/576; 356/208
[51] Int. Cl.².......................................... G01N 21/26
[58] Field of Search ........... 250/573, 576, 574, 564; 356/208, 201, 207

[56] References Cited
UNITED STATES PATENTS

| | | |
|---|---|---|
| 3,207,026 | 9/1965 | Churchill et al. .................... 356/206 |
| 3,268,734 | 8/1966 | Bjorn ................................. 250/564 |
| 3,700,330 | 10/1972 | Davis ................................. 250/574 |
| 3,790,289 | 2/1974 | Schmidt et al...................... 356/207 |
| 3,826,918 | 7/1974 | Van der Koogh et al. ......... 250/343 |

*Primary Examiner*—Walter Stolwein
*Attorney, Agent, or Firm*—Flynn and Frishauf

[57] ABSTRACT

To test optical transmissivity of exhaust gases from internal combustion engines without requiring cleaning of confining walls of pipes or tubes, a film of liquid is caused to adhere to the inner surface of a transparent tube or pipe section by rotating the tube or pipe section so that the film will remain at the inner wall due to centrifugal force; light is transmitted transversely of the pipe section and through the exhaust gas. The liquid is preferably continually renewed by applying fresh liquid to the inside of the rotating pipe section, excess liquid being removed from an overflow ridge.

16 Claims, 3 Drawing Figures

ANALYZING GASES BY TESTING THE OPTICAL CHARACTERISTICS OF EXHAUST GASES FROM INTERNAL COMBUSTION ENGINES

CROSS REFERENCE TO RELATED APPLICATION

U.S. Ser. No. 579,463, filed May 21, 1975, assigned to the assignee of the present application.

The present invention relates to testing of the exhaust gases of internal combustion engines, and particularly of gases which have contaminant particles therein which are apt to form deposits on confining walls, thereby falsifying test results when shining light through a transparent pipe section, and generally to test the optical characteristics of gases which have particles contained therein apt to precipitate or deposit on the walls of confining tubes or pipes.

It has previously been proposed to optically measure the characteristics of gases by shining light transversely through gases emitted from an operating internal combustion engine, or arising during other continuous processes. Due to contamination of the measuring instrument by the gases themselves, typically soot, and other carbon particles contained in the exhaust gases from internal combustion engines, flues, and the like, it has been found practically impossible to continuously test the optical characteristics of the gas. Devices were required which had to be cleaned in frequent intervals; the cleaning devices themselves had to be maintained and could be used only for short periods of time without servicing.

Various other measuring methods and systems had been proposed which, however, did not operate continuously. Test samples were derived from the exhaust gases of the internal combustion engine, to be analyzed by various methods which usually required much time and apparatus. It has also been proposed to capture particles of carbon or soot on filter paper and then to optically evaluate the blackening of the filter paper itself.

It is an object of the present invention to provide an apparatus to optically determine the attenuation of light or other radiation, when passing through gases, typically the exhaust gases from internal combustion engines, which permits continuous operation and provides reproducible test results of uniform accuracy, while avoiding the necessity of frequent maintenance, cleaning and service. The apparatus should, preferably, be easily maintained, reliable, and should be capable of application to standard exhaust systems from internal combustion engines, while requiring but little attention from operating personnel.

SUBJECT MATTER OF THE PRESENT INVENTION

Briefly, a pipe section transparent to radiation, typically light, is located in the flowing stream of gases; the inner wall of the pipe section has a film of liquid applied thereto which adheres to the pipe section by centrifugal force. Preferably, the pipe section is rotated, either by an external motor, or by the liquid itself directed thereagainst at an angle. The radiation, typically light, is passed transversely through the pipe section, the film of liquid thereon, and the gas stream, to be received at the other side of the pipe section by a receiver, such as a photoelectric pick-up. The attenuation of the light received by the photoelectric pick-up then is measure of the clouding of the gas. The liquid may be water and, preferably, is continuously renewed, for example being recycled through a filter.

Contamination, or deposition of dirt, soot particles, and the like, on confining walls of the gas in the region of measurement is almost completely avoided by the cleaning effect of the liquid film adhering to the inner wall of the transparent pipe section. The measuring results are therefore hardly influenced by dirt deposition on the transparent walls of this pipe section. The apparatus can be used for any optical measurement; the pipe section which is made transparent or translucent can be selected to have practically any desired size. It is possible to measure the clouding of the entire gas stream and not only a portion or bled-off sample thereof, thus additionally decreasing further sources of error. With little apparatus, a continuous measurement of the optical characteristics of exhaust gases can be obtained, not only under static conditions, but also under dynamic conditions; thus, the change in carbon content upon transition of operation of an internal combustion engine from steady state to acceleration, or to externally powered operation can be measured.

In accordance with a feature of the present invention, the transparent pipe section is a short rotatable stub which is directly connected to the exhaust pipe of an internal combustion engine, or which forms part of the exhaust pipe thereof. Hardly any service is required due to the self-cleaning effect. The short stubby arrangement and the simple matching of diameters of the transparent pipe section to existing exhaust pipes does not interfere with gas flow, and reactive effects of pipe sections such as oscillation, wave reflection, or resonance phenomena which react to the engine are effectively avoided. The flow conditions are good; changes such as increased or decreased diameters through which the gases must pass upon being measured are avoided, so that no pressure losses not inherent in the overall length of the pipe will be experienced, and there will be no sedimentation of soot aerosols.

In accordance with a preferred feature of the invention, the portion of the pipe which is transparent and which is rotatable is formed as a hollow shaft located in line with the exhaust gas. This arrangement particularly facilitates mechanical construction and provides for excellent gas flow characteristics therethrough.

The liquid which flows along the inner wall of the measuring section is preferably clear, for example water, and adhered thereto by centrifugal force, while being continuously renewed during operation. This continuous renewal of the liquid enhances the self-cleaning effect and deterioration of measuring results due to increasing contamination of the liquid itself is avoided.

The hollow shaft preferably is formed at the inside with a ring groove, to one side of which fresh liquid is applied, and the downstream side of which is formed with an overflow ridge. The ring groove then will always maintain the liquid at a predetermined thickness and width — corresponding to the depth and width of the groove — so that the extent of the liquid film will always be constant.

The rotatable element preferably consists of "Plexiglas" (a polymethacrylate acid ester). "Plexiglas" has some advantageous properties, particularly adapted for use in the present invention, such as high light transmissivity, a smooth surface which is easily polished and thus easily cleaned, chemical inertness and ease of manufacture and working.

The rotatable section can be rotated in various ways; a particularly simple drive is a friction wheel drive from the outside. The rotatable section may, however, also be rotated by the fluid itself, if the fluid is applied through a nozzle engaging at the inside of the rotatable section at an angle in the direction of rotation, similarly to rotation generation in centrifugal filters. In another form, the rotatable element may be supplied with external magnets which are subjected to inductive fields, similarly to permanent magnet electric motors.

The invention will be described by way of example with reference to the accompanying drawings, wherein.

Figure 1:
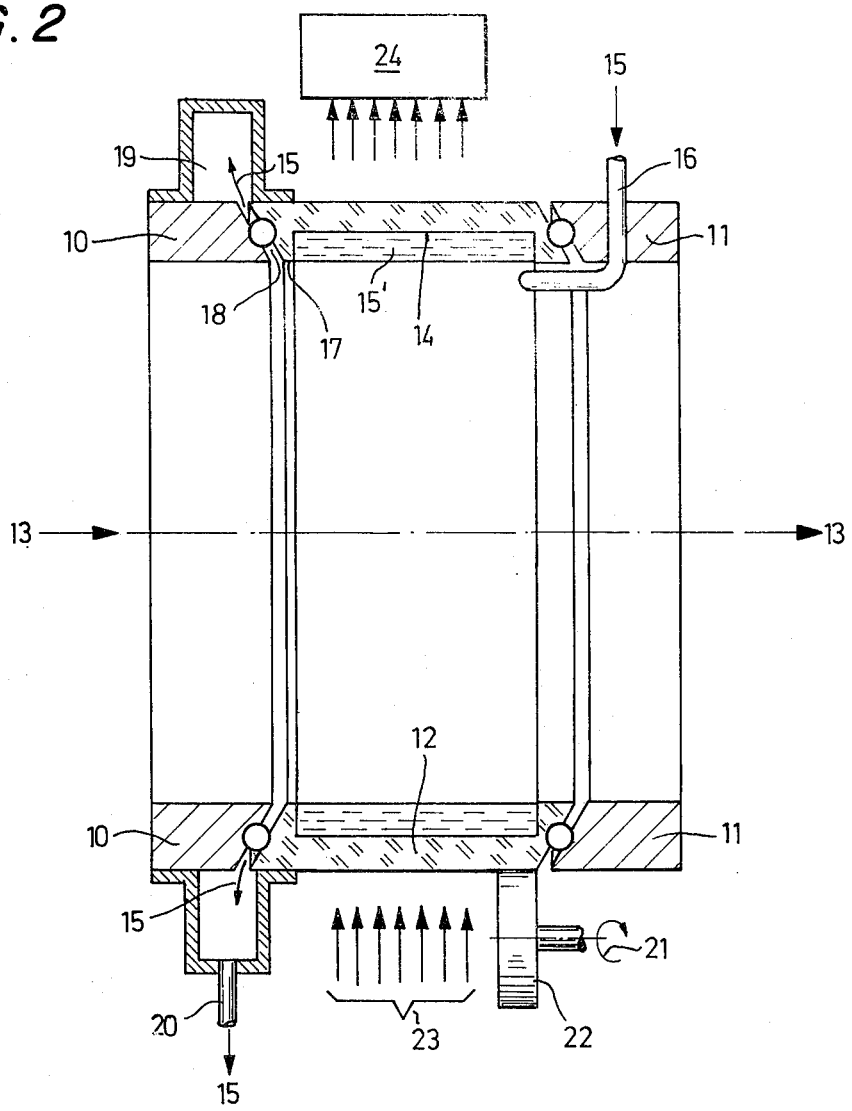
FIG. 1 is a schematic longitudinal section of the apparatus using, and in accordance with, the present invention.

The exhaust system of an automotive vehicle is formed with two spaced flanges 10, 11. The internal combustion engine of the vehicle and the remainder of the system are not shown. A hollow shaft 12 made of radiation-transmissive material, typically light transmissive, and hence transparent plastic material such as "Plexiglas", is located between the flanges 10, 11. The flanges are held in spaced position, as shown in FIG. 1, by a suitable frame structure, not shown. The exhaust gas, the center line of which is indicated by a chain-dotted arrow line 13 flows in the direction of the arrows through the exhaust pipe, from flange 10 through transparent section 12 to flange 11 and hence to the remainder of the exhaust system and to ambient air.

A ring-shaped groove 14 is formed in the interior of the hollow shaft 12. The groove 14 extends over almost the entire width of the shaft 12. In operation, the hollow shaft 12, which actually forms a sleeve or pipe section, is rotated rapidly. A liquid 15 is introduced through a pipe 16 passing through flange 11 and extending into the transparent section 12. Liquid is continuously introduced through pipe 16, and due to rotation of shaft 12 will be centrifugally adhered at the inner wall of the section 12, within the groove 14. The liquid will flow over the overflow edge 17 at the side remote from pipe 16, to be drained through a gap 18 and collected in a collection manifold 19 for removal by a pipe 20. The liquid 15 may then be passed through a filter, to be cleaned, and re-circulated back to pipe 16. The re-circulation path is not shown and may include any suitable and well-known structure.

The drive comprises a friction wheel 22 which is rapidly rotated as schematically shown by the arrow 21. Frictional engagement between wheel 22 and section 12 which, as shown, is held between the flanges 10, 11 in ball bearings, causes section 12 likewise to rotate rapidly. The liquid 15, for example water, introduced through pipe 16 causes adhesion at the inner wall of the section 12 due to centrifugal force, while also being subject to some axial flow due to continuous renewal from pipe 16 and drainage through overflow edge 17. The inner wall of the groove 14 of the pipe section 12 is not contacted by the gases at all, and thus is maintained completely clean by the film 15' of liquid.

Light, preferably visible light but which may be IR or UV or other radiation, is transmitted across the section 12, as schematically indicated by arrows 23, transmitting light into the wall of section 12, through the film 15, through the gas, through the second film of liquid and through the other wall, to be received in a radiation measuring instrument, such as a photoelectric cell or other photo-responsive transducer 24. Clouding, or darkening, of the exhaust of the gas stream 13 causes changes in the received light on transducer 24, which changes are representative of the optical characteristics of the gas stream. The measured values obtained from transducer 24 can be used particularly to determine the content of carbon or soot in the exhaust of the internal combustion engines.

The exhaust gases are thus not carried along a fixed wall or confining surface; rather, in the optically effective range a liquid wall is used which, due to continuous flow conditions is maintained continuously in clean state. The liquid wall is generated by rotating the section 12. The constant renewal of liquid 15, causing axial flow of the liquid within the groove 14, additionally cleans the inner wall of the section 12 and removes any particles or components of the exhaust gas which might have deposited or precipitated at the inner wall within the transparent region through which the light beams 23 are directed to transducer 24. Thus, not only is the liquid constantly renewed by clean liquid; the flow of liquid also cleans the inner surface of the transparent region.

The present invention has been described particularly in connection with optical evaluation of the blackening or clouding of exhaust gases from internal combustion engines. Other optical measuring systems may be used, such as scattering of a predetermined beam of light, color evaluation, formation of shadows, as well as use of different light sources, such as lasers; luminescence phenomena in the gases may also be evaluated. Depending on the structure of the light being applied, and on the transducers, fiber optics may be used to advantage. The light source, as well as the receiving transducer, may be connected in a self-balancing loop.

Figure 2:
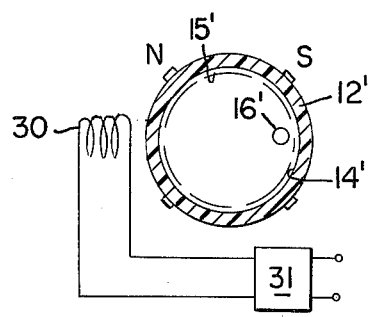
FIG. 2 is a highly schematic transverse cross-sectional view through the measuring section and illustrating an electrical external motor drive.
Figure 3:
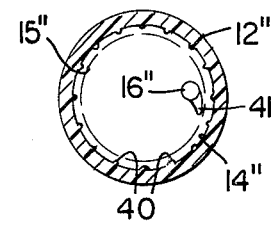
FIG. 3 is a schematic transverse sectional view illustrating a hydraulic drive.

The hollow, transparent pipe section 12 can be driven in various ways. As shown in FIG. 2, hollow section 12' has permanent magnet elements N, S mounted thereon, subjected to an electrical field generated by a coil 30, the energization of which is controlled by a control source 31, similarly to motor controls for brushless, permanent magnet d-c motors, and which are well known; the shaft 12 may also be constructed to form the shaft of a small pancake or axial air gap-type permanent magnet motor, in which stator windings are located in a plane transverse to the central axis of the rotating pipe section 12', forming the shaft thereof. FIG. 3 illustrates hydraulic drive. The inlet pipe section 16" is formed with a nozzle 41 extending tangentially at the inside of groove 14". Preferably, at least the region beneath the nozzle 41 of groove 14" is formed with small ridges 40, which may be spiralled and extend over the length of the groove 14", to enhance rotation of the pipe section 12", while contributing to axial flow and the cleaning effect.

All types of gases which have compounds, components, or particles therein which are apt to deposit or precipitate on the outside walls of a confining pipe can be analyzed. Particularly, exhaust gases from automotive vehicles, from furnaces, flues, smoke pipes, and the like, can be tested. Measurement of dust contamination or other particle contents in gases can also be carried out.

Various changes and modifications may be made within the scope of the inventive concept.

We claim:
1. In an apparatus to determine the soot content in the exhaust gases (13) of an internal combustion engine, a gas optical transmissivity analysis system connected into the exhaust stream of the engine, said system comprising
   a rotatable tubular element (12) of material transparent to radiation, connected in the stream of the gas (13);
   means (15, 16) introducing a liquid transparent to radiation to the inside wall of the tubular element (12) to form a film (15) of liquid thereon by centrifugal force upon rotation of said element;
   means (23) directing radiation across said tubular element (12) through the liquid film (15) centrifugally adhering to the inner wall of the tubular element (12) and through the gas stream flowing therein;
   and means (24) analyzing the radiation received after having passed through said stream to provide a measure representative of the optical characteristics of the gas flowing through the tubular element (12) and hence of the soot content of the exhaust gas.

2. System according to claim 1, wherein the tubular element (12) is optically transparent, the liquid is essentially optically transparent, and the radiation is light.

3. System according to claim 1, wherein the tubular rotatable element (12) comprises a hollow shaft section rotatably located in the exhaust gas line (10, 11) of the internal combustion engine.

4. System according to claim 1, wherein the means introducing a liquid into the tubular element (12) comprises means (16) feeding fresh liquid to the rotatable element during rotation thereof and means (17, 18, 19, 20) draining liquid therefrom, the liquid flowing axially along said tubular element while being adhered to the inner wall thereof by centrifugal action upon rotation thereof.

5. System according to claim 4, wherein the tubular element (12) is formed with a ring-shaped groove (14) terminating in a lateral overflow ridge (17) and wherein the means introducing the liquid comprises a fixed pipe terminating adjacent the ring groove at the side remote from the overflow ridge (17) to supply liquid (15) to the ring groove (14) at the inner surface of the tubular element (12) and permit flow of the liquid, adhered by centrifugal action in the ring groove to the overflow ridge, the liquid filling the ring groove.

6. System according to claim 2, wherein the tubular element (12) comprises a transparent plastic.

7. System according to claim 1, further comprising motor drive means operatively connected to said tubular element to rotate said element.

8. System according to claim 7, wherein said motor drive means comprises an external friction roller (22) engaging said tubular element (12).

9. System according to claim 7, wherein said drive means comprises a hydraulic drive (16'', 41, 40) including means (41) directing said liquid against the rotatable tubular element (12'') in a direction to rotate the same.

10. System according to claim 7, wherein said drive means are electric motor drive means (N, S; 30, 31).

11. Gas analysis apparatus comprising the system of claim 1 to determine the optical properties of a flowing gas in which the gas includes components which have the tendency to precipitate, or deposit on or to contaminate walls confining the gas.

12. Method of testing the exhaust gas of an internal combustion engine for soot and other particles which cause attenuation of light passing through the stream of the exhaust gas including a method of analysis of a flowing gas to determine the characteristics of the gas stream when subjected to radiation passing therethrough comprising
   confining the gas stream in a cylindrical pipe or tube (12) by passing the stream therethrough;
   introducing a liquid transparent to the radiation adjacent the inside wall of the confining pipe or tube;
   rotating the liquid to centrifugally adhere the liquid to the wall of the confining pipe or tube and form a film of liquid thereon and prevent precipitation or deposits on the walls of the pipe or tube;
   passing said radiation through the pipe, the film of liquid, and across the flowing stream of gas;
   and analyzing the radiation after it has passed twice through the pipe, twice through the film of liquid, and across the flowing stream of gas.

13. Method according to claim 12, wherein the step of rotating the liquid comprises rotating the confining pipe or tube, and the step of introducing the liquid comprises introducing the liquid adjacent the pipe or tube, so that the liquid will adhere to the tube and form a film thereon upon rotation of the pipe or tube.

14. Method according to claim 13, wherein the step of introducing the liquid comprises continuously introducing liquid to the rotating pipe or tube;
   and the method further comprises the step of continuously removing liquid from the pipe or tube to maintain a flow of fresh liquid thereto, adhering to the wall of the pipe or tube by centrifugal action and flowing axially from the introduction zone to the removal zone.

15. Method according to claim 12, wherein the pipe or tube is made of light-transmissive material, the liquid is essentially light-transmissive, and the radiation is light.

16. Method comprising the gas analysis method of claim 11 of continuous analysis of a flowing gas including components which have the tendency to form deposits or precipitates on the walls of the confining pipe or tube for the gas.

* * * * *